United States Patent [19]

Jinbo et al.

[11] 4,421,919
[45] Dec. 20, 1983

[54] 4-OXIMINO-1,2,3,4-TETRAHYDROQUINO-LINE DERIVATIVES

[75] Inventors: Susumu Jinbo; Shoichi Kohno; Koichi Kashima, all of Tokyo, Japan

[73] Assignees: Hodogaya Chemical Co., Ltd.; Mochida Seiyaku Kabushiki Kaisha, both of Tokyo, Japan

[21] Appl. No.: 281,243

[22] Filed: Jul. 7, 1981

[30] Foreign Application Priority Data

Jul. 28, 1980 [JP] Japan ............................ 55-103272
Jul. 28, 1980 [JP] Japan ............................ 55-103273
Mar. 19, 1981 [JP] Japan ............................ 56-39909
Mar. 19, 1981 [JP] Japan ............................ 56-39910
Mar. 19, 1981 [JP] Japan ............................ 56-39911

[51] Int. Cl.³ ............... C07D 215/48; C07D 215/42; A61K 31/47
[52] U.S. Cl. ........................... 546/159; 424/258; 542/439
[58] Field of Search ............ 424/258; 546/159; 542/439

[56] References Cited

U.S. PATENT DOCUMENTS 3,509,171  4/1970  Welstead, Jr. et al. ...... 546/169 X
4,013,662  3/1977  Harbert ..................... 424/258 X

FOREIGN PATENT DOCUMENTS 55-122719  9/1980  Japan ........................... 424/258
56-53614   5/1981  Japan ........................... 424/258

OTHER PUBLICATIONS

Johnson et al., J. Am. Chem. Soc., vol. 71, (6), pp. 1901–1905, (1949).
Hromatka et al., Chemical Abstracts, vol. 67, 73532t, (1967).
Onishi et al., Chemical Abstracts, vol. 95, 215126t, (1981).
Johnson et al., J. Am. Chem. Soc., vol. 75, pp. 2766–2768, (1953).

Primary Examiner—Diana G. Rivers
Attorney, Agent, or Firm—Parkhurst & Oliff

[57] ABSTRACT 4-oximino-1,2,3,4-tetrahydroquinoline derivatives of the formula (I):

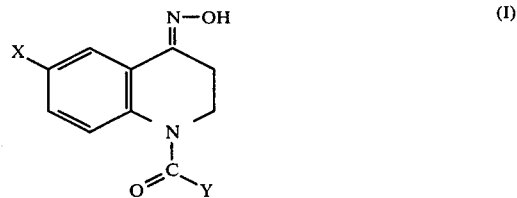

wherein X represents a halogen atom and Y represents a hydrogen atom, a straight-chain or branched-chain alkyl group, a halogen-substituted lower alkyl group, a phenylalkyl group, a phenylalkenyl group, an unsubstituted or halogen-substituted phenyl group, a nitrogen-containing aromatic group, a straight-chain or branched-chain alkoxy group or an alkyl-substituted or phenyl-substituted amino group.

5 Claims, No Drawings

4-OXIMINO-1,2,3,4-TETRAHYDROQUINOLINE DERIVATIVES

BACKGROUND OF THE INVENTION

1. Field of the Invention

This invention relates to a novel 4-oximino-1,2,3,4-tetrahydroquinoline derivative having antiedemic, diuretic and hypotensive effects.

2. Description of the Prior Art

Extensive research has been continued for developing efficient antiphlogistic analgesics which are neutral or basic and therefore do not cause gastrointestinal disorders, ever since non-steroid anti-inflammatory agents, particularly acidic non-steroid anti-inflammatory agents, were found to cause severe gastrointestinal disorders.

The present inventors, after many years of research, have found a novel 4-oximino-1,2,3,4-tetrahydroquinoline derivative which exhibits strong antiedemic, diuretic and hypotensive effects without causing appreciable gastrointestinal disorders, thus achieving this invention.

SUMMARY OF THE INVENTION

Accordingly, this invention provides a novel 4-oximio-1,2,3,4-tetrahydroquinoline derivative of the general formula:

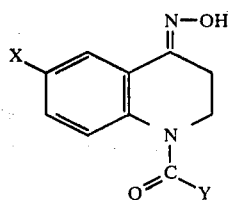

(I)

wherein X represents a halogen atom and Y represents a hydrogen atom, a straight-chain or branched-chain alkyl group, a halogen-substituted lower alkyl group, a phenylalkyl group, a phenylalkenyl group, an unsubstituted or halogen-substituted phenyl group, a nitrogen-containing aromatic group, a straight-chain or branched-chain alkoxy group or an akyl-substituted or phenyl-substituted amino group.

DESCRIPTION OF THE PREFERRED EMBODIMENT

The compounds of this invention having the formula (I) may be generally produced as follows:

6-Halogen-substituted-4-oxo-1,2,3,4-tetrahydroquinolines, the intermediates in the production of the compounds of this invention, may be produced by a known method, such as a method described in J. Medicinal Chem., 8, 566–571, as follows:

A p-halogen-substituted aniline of the formula:

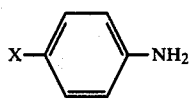

wherein X represents a halogen atom; and an acrylic acid ester of the formula:

CH$_2$=CHCOOR wherein R is an ester forming group are subjected to Michael condensation reaction under heating in a solvent such as benzene, toluene, ethyl acetate, ethanol etc. or, if desired, using a base such as sodium hydride, a sodium alkoxide, etc. at room temperature or at an elevated temperature, to obtain a 3-(p-halogen-substituted phenylamino)propionic acid ester of the formula:

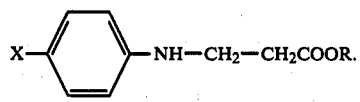

The ester compound thus obtained is hydrolyzed and subsequently heated using phosphorus pentoxide, polyphosphoric acid or the like as a dehydrating agent in the presence or the absence of a solvent such as benzene, toluene, xylene, etc., whereby a 6-halogen-substituted-4-oxo-1,2,3,4-tetrahydroquinoline of the formula:

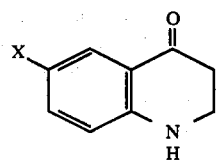

is synthesized.

Alternatively, β-propiolactone is condensed with a p-halogen-substituted aniline with or without a Lewis acid catalyst such as zinc chloride, aluminum chloride, etc., in the presence of a solvent such as acetonitrile, to produce a 3-(p-halogen-substituted phenylamino)propionic acid, which is then cyclized with dehydration using phosphorus pentoxide, polyphosphoric acid or the like or, after converting the carboxyl group to the acid chloride and subjecting to cyclization by Friedel-Crafts reaction, the 6-halogen-substituted-4-oxo-1,2,3,4-tetrahydroquinoline can be obtained as the intermediate.

Thereafter, in order to effect the N-acylation of the above-obtained intermediate, 6-halogen-substituted-4-oxo-1,2,3,4-tetrahydroquinoline, this is reacted with a reactive derivative of a carboxylic acid, for example, an acid anhydride, acid chloride or acid bromide of a carboxylic acid of the formula:

(Y'CO)$_n$A wherein Y' represents a hydrogen atom, a straight-chain or branched-chain alkyl group, a halogen-substituted lower alkyl group, a phenylalkyl group, a phenylalkenyl group, an unsubstituted or halogen-substituted phenyl group or a nitrogen-containing aromatic group; A represents —Cl, —Br, or —O—; and n represents 2 when A is —O— or 1 when A is —Cl or —Br; in the presence of an organic base such as triethylamine, pyridine, etc., in a solvent such as ether, tetrahydrofuran, dioxane, chloroform, benzene, etc., to obtain an N-substituted-6-halogen-substituted-4-oxo-1,2,3,4-tetrahydroquinoline derivative of the formula:

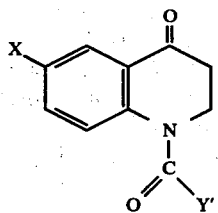

wherein X represents a halogen atom and Y' is as defined above.

Alternatively, it is also possible to react said reactive derivative of the carboxylic acid with an alkali metal amide of the above-described intermediate (e.g. sodium, potassium or lithium amide, etc.) in such a solvent as described above to obtain the N-substituted-6-halogen-substituted-4-oxo-1,2,3,4-tetrahydroquinoline derivatives.

In order to introduce a carbamoyl group in said intermediate, phosgene gas is passed into said intermediate in the presence of a solvent such as tetrahydrofuran, dioxane, ether, chloroform, etc., or, after the introduction of phosgene gas, an organic base such as triethylamine, pyridine, etc., is added dropwise to the mixture to give a 6-halogen-substituted-4-oxo-1-chloroformyl-1,2,3,4-tetrahydroquinoline, which product is then reacted with an amine of the formula:

wherein R' represents an alkyl group or a phenyl group and R" represents a hydrogen atom or the same meaning as assigned to R'; to obtain a N-substituted-6-halogen-substituted-4-oxo-1,2,3,4-tetrahydroquinoline derivative of the formula:

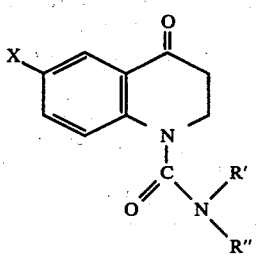

wherein X represents a halogen atom and R' and R" are as defined above.

When N-alkoxycarbonylation of the above-described intermediate is desired, this is reacted with a chloroformate of the formula:

ROCOCl wherein R is a straight-chain or branched-chain alkyl group; in the presence of an organic base such as triethylamine, pyridine, etc., in a solvent such as ether, tetrahydrofuran, dioxane, dichloromethane, chloroform, benzene etc., to obtain a N-substituted-6-halogen-substituted-4-oxo-1,2,3,4-tetrahydroquinoline derivative of the formula:

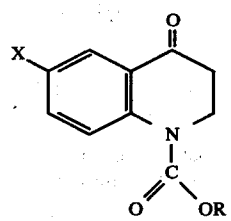

wherein X represents a halogen atom and R is as defined above.

Alternatively, it is also possible to react said chloroformate with an alkali metal amide (e.g. sodium, potassium or lithium amide, etc.) of the 6-halogen-substituted-4-oxo-1,2,3,4-tetrahydroquinoline.

The N-substituted-6-halogen-substituted-4-oxo-1,2,3,4-tetrahydroquinoline derivative thus synthesized is then heated together with hydroxylamine hydrochloride in an appropriate organic solvent, for example, a mixed solvent of pyridine-alcohol, triethylamine-alcohol, pyridine-tetrahydrofuran, pyridinedioxane, and triethanolamine-alcohol, thereby the N-substituted-6-halogen-substituted-4-oximino-1,2,3,4-tetrahydroquinoline derivative of this invention may be obtained.

The term "halogen atom" as used herein means a chlorine atom, a bromine atom or a fluorine atom.

The thus obtained compounds according to this invention which are represented by the general formula I have strong antiedemic, diuretic and hypotensive effects and hardly cause gastrointestinal disorder, and therefore they are excellent as pharmaceutical drugs.

Accordingly, the compounds of this invention may be formulated into pharmaceutical products, either alone or in combination with other pharmacologically active compounds, and if desired, also with binding agents, fillers, flavors, etc., commonly employed in the pharmaceutical field in a suitable conventional manner.

This invention is illustrated by the following examples, in which the parts and % represent parts by weight and % by weight respectively.

EXAMPLE 1

Synthesis of 6-chloro-4-oximino-1-formyl-1,2,3,4-tetrahydroquinoline 18.16 parts of 6-chloro-4-oxo-1,2,3,4-tetrahydroquinoline and 150 parts of formic acid (purity of 98% or higher) were mixed and reacted under reflux with stirring for 3 hours.

The reaction mixture was distilled under reduced pressure to remove the excess formic acid, 100 ml of ethanol was added to the residue and heated to dissolve it. After cooling, the precipitated crystals were filtered out, and dried to obtain 18.03 parts of 6-chloro-4-oxo-1-formyl-1,2,3,4-tetrahydroquinoline.

Then, the above product was dissolved in 270 ml of ethanol, to which were added 15.0 parts of hydroxylamine hydrochloride and 17.0 parts of pyridine, and the reaction was effected under reflux for 1.5 hours.

The reaction mixture was poured into one liter of water, filtered out, washed with water, dried, and recrystallized from ethanol to obtain 18.3 parts of 6-chloro-4-oximino-1-formyl-1,2,3,4-tetrahydroquinoline as white crystals.

This product showed a melting point of 192°–193° C. when measured by the method specified in the Japanese Pharmacopeia, and the results of its elemental analysis were as follows:

Elemental Analysis:

|  | C | H | Cl | N |
|---|---|---|---|---|
| Calculated: | 53.45 | 4.01 | 15.81 | 12.47 |
| Found: | 53.41 | 4.00 | 15.79 | 12.50. |

EXAMPLE 2

Synthesis of 6-chloro-4-oximino-1-acetyl-1,2,3,4-tetrahydroquinoline 18.16 parts of 6-chloro-4-oxo-1,2,3,4-tetrahydroquinoline and 11.23 parts of acetic anhydride were mixed and reacted at 90° C. with stirring for 3 hours.

The reaction mixture was poured into 300 ml of water, and the precipitated crystals were filtered out, washed with water, and dried to obtain 20.1 parts of 6-chloro-4-oxo-1-acetyl-1,2,3,4-tetrahydroquinoline.

Then, the above product was dissolved in 300 ml of ethanol, to which were added 15.64 parts of hydroxylamine hydrochloride and 17.8 parts of pyridine, and the reaction was effected under reflux for 1.5 hours. Thereafter, the product was treated as in Example 1 to obtain 20.4 parts of 6-chloro-4-oximino-1-acetyl-1,2,3,4-tetrahydroquinoline as white crystals.

This product showed a melting point of 214°–215.5° C. when measured by the method specified in the Japanese Pharmacopeia, and the results of its elemental analysis were as follows:

Elemental analysis:

|  | C | H | Cl | N |
|---|---|---|---|---|
| Calculated: | 55.35 | 4.61 | 14.88 | 11.74 |
| Found: | 55.40 | 4.65 | 14.85 | 11.71. |

EXAMPLE 3

Synthesis of 6-chloro-4-oximino-1-propionyl-1,2,3,4-tetrahydroquinoline 18.16 parts of 6-chloro-4-oxo-1,2,3,4-tetrahydroquinoline, 24.0 parts of pyridine and 100 ml of dioxane were mixed, and 11.1 parts of propionyl chloride was added dropwise to the mixture with stirring while the temperature was maintained at 0°–5° C. After addition, the reaction was conducted at room temperature for 5 hours.

The reaction mixture was poured into one liter of water, the precipitated crystals were filtered out, washed with water and then with petroleum ether, and dried to obtain 20.4 parts of 6-chloro-4-oxo-1-propionyl-1,2,3,4-tetrahydroquinoline.

Thereafter, the above product was converted to the oxime as in Example 1, thereby obtaining 20.6 parts of white 6-chloro-4-oximino-1-propionyl-1,2,3,4-tetrahydroquinoline. This product showed a melting point of 166°–169° C. when measured by the method specified in the Japanese Pharmacopeia, and the results of its elemental analysis were as follows:

Elemental Analysis:

|  | C | H | Cl | N |
|---|---|---|---|---|
| Calculated: | 57.03 | 5.15 | 14.06 | 11.09 |
| Found: | 56.98 | 5.09 | 14.01 | 11.10 |

EXAMPLES 4–15

In each example, the desired product was obtained by the method described in Example 3, except that the propionyl chloride was replaced by the corresponding acid chloride. The properties of the products are given in Table 1 below.

EXAMPLE 16

Synthesis of 6-chloro-4-oximino-1-methylcarbamoyl-1,2,3,4-tetrahydroquinoline (a) 54.5 parts of 6-chloro-4-oxo-1,2,3,4-tetrahydroquinoline and 300 parts of dioxane were mixed, and 44.6 parts of phosgene were introduced to the stirred mixture over about 30 minutes while the temperature was maintained at 20°–25° C. After the introduction, the temperature was raised gradually, and the reaction was effected at 40°–45° C. for 2.5 hours, after which the temperature was further raised to 70° C., nitrogen gas was passed through the mixture, and the solvent (dioxane) was distilled off under reduced pressure.

Petroleum ether was added to the residue followed by filtration, washing and drying, and there was obtained 70.3 parts of 6-chloro-4-oxo-1-chloro-formyl-1,2,3,4-tetrahydroquinoline (m.p. 114°–116° C.).

(b) 2.6 Parts of the above product was dissolved in 30 ml of dioxane, and this solution was added dropwise to 10 ml of dioxane solution containing 1.0 part of monomethylamine while maintaining at 0°–5° C. After the addition, stirring was conducted at room temperature for 4 hours.

The reaction mixture was poured into water, and the precipitated crystals were filtered out, washed with water and then with petroleum ether, dried, and recrystallized from a mixed solvent of ethanol-n-hexane to obtain 2.2 parts of 6-chloro-4-oxo-1-methylcarbamoyl-1,2,3,4-tetrahydroquinoline. This product was dissolved in 30 ml of ethanol, to which were added 2.0 parts of hydroxylamine hydrochloride and 2.2 parts of pyridine, and the reaction was conducted under reflux for 2 hours. Thereafter, the mixture was treated as described in Example 1 to obtain 2.2 parts of white crystals of 6-chloro-4-oximino-1-methylcarbamoyl-1,2,3,4-tetrahydroquinoline. This product showed a melting point of 211°–212° C. when measured by the method specified in the Japanese Pharmacopeia, and the results of its elemental analysis were as follows:

Elemental Analysis:

|  | C | H | Cl | N |
|---|---|---|---|---|
| Calculated: | 52.07 | 4.73 | 14.00 | 16.57 |
| Found: | 52.05 | 4.75 | 13.97 | 16.49 |

EXAMPLES 17–19

In each example, the 6-chloro-4-oxo-1-chloroformyl-1,2,3,4-tetrahydroquinoline obtained in (a) of Example 16 (a) was treated as described in Example 16 (b) except that the monomethylamine in (b) of Example 16 was replaced by the corresponding amine or aniline, to obtain the desired product. The properties of the products are given in Table 1 below.

solvent(dichloromethane)was distilled off under reduced pressure, and 100 ml of ethanol was added to the residue and heated to dissolve it. After cooling, the

TABLE 1

| Example No. | Compound | Appearance | Melting point (°C.) |
|---|---|---|---|
| 4 | 6-Chloro-4-oximino-1-butyryl-1,2,3,4-tetrahydroquinoline | White crystal | 141–142 |
| 5 | 6-Chloro-4-oximino-1-isobutyryl-1,2,3,4-tetrahydroquinoline | " | 185–186 |
| 6 | 6-Chloro-4-oximino-1-valeryl-1,2,3,4-tetrahydroquinoline | " | 118–120 |
| 7 | 6-Chloro-4-oximino-1-isovalerylacetyl-1,2,3,4-tetrahydroquinoline | " | 142–143 |
| 8 | 6-Chloro-4-oximino-1-trimethylacetyl-1,2,3,4-tetrahydroquinoline | " | 204–208 |
| 9 | 6-Chloro-4-oximino-1-hexanoyl-1,2,3,4-tetrahydroquinoline | " | 153–154 |
| 10 | 6-Chloro-4-oximino-1-heptanoyl-1,2,3,4-tetrahydroquinoline | " | 156–158 |
| 11 | 6-Chloro-4-oximino-1-octanoyl-1,2,3,4-tetrahydroquinoline | " | 147–149 |
| 12 | 6-Chloro-4-oximino-1-phenylacetyl-1,2,3,4-tetrahydroquinoline | " | 181–183 |
| 13 | 6-Chloro-4-oximino-1-cinnamoyl-1,2,3,4-tetrahydroquinoline | " | 216–217 |
| 14 | 6-Chloro-4-oximino-1-trifluoroacetyl-1,2,3,4-tetrahydroquinoline | " | 158–159 |
| 15 | 6-Chloro-4-oximino-1-nicotinyl-1,2,3,4-tetrahydroquinoline | " | 227–228 |
| 17 | 6-Chloro-4-oximino-1-ethylcarbamoyl-1,2,3,4-tetrahydroquinoline | " | 183–184 |
| 18 | 6-Chloro-4-oximino-1-dimethylcarbamoyl-1,2,3,4-tetrahydroquinoline | " | 150–152 |
| 19 | 6-Chloro-4-oximino-1-phenylcarbamoyl-1,2,3,4-tetrahydroquinoline | " | 182.5–183.5 |

EXAMPLE 20

18.16 Parts of 6-chloro-4-oxo-1,2,3,4-tetrahydroquinoline, 10.3 parts of pyridine and 100 ml of dioxane were mixed, and 12.3 parts of methyl chloroformate were added dropwise to the mixture with stirring while the temperature was maintained at 0°–5° C. After the addition, the reaction was conducted at room temperature for 5 hours.

The reaction mixture was poured into one liter of water, the precipitated crystals were filtered out, washed with water and then with n-hexane, and dried to obtain 22.0 parts of 6-chloro-4-oxo-1-methoxycarbonyl-1,2,3,4-tetrahydroquinoline.

Thereafter, the above product was dissolved in 330 ml of ethanol, to which were added 15.0 parts of hydroxylamine hydrochloride and 17.0 parts of pyridine, and the reaction was conducted under reflux for 2 hours.

The reaction mixture was poured into one liter of water, filtered out, washed with water, dried, and recrystallized from ethanol to obtain 19.9 parts of white crystals of 6-chloro-4-oximino-1-methoxycarbonyl-1,2,3,4-tetrahydroquinoline. The product showed a melting point of 162°–163° C. when measured by the method specified in the Japanese Pharmacopeia, and the results of its elemental analysis were as follows:

Elemental Analysis:

| | C | H | Cl | N |
|---|---|---|---|---|
| Calculated: | 51.87 | 4.32 | 13.95 | 11.00 |
| Found: | 51.85 | 4.35 | 13.88 | 11.02. |

EXAMPLE 21

16.51 parts of 6-fluoro-4-oxo-1,2,3,4-tetrahydroquinoline, 10.3 parts of pyridine and 100 ml of dichloromethane were mixed, and 14.2 parts of ethyl chloroformate were added dropwise to the mixture with stirring while the temperature was maintained at 0°–5° C. After the addition, the reaction was conducted at room temperature for 5 hours.

500 ml of cold water was poured into the reaction mixture, and the layers were separated. The organic phase was washed once with 100 ml of a 1 N aqueous hydrochloric acid and then twice with 100 ml each of water, and dried over anhydrous Glauber's salt. The precipitated crystals were filtered out, and dried to obtain 20.8 parts of 6-fluoro-4-oxo-1-ethoxycarbonyl-1,2,3,4-tetrahydroquinoline.

Then, the above product was dissolved in 310 ml of ethanol, to which were added 14.3 parts of hydroxylamine hydrochloride and 16.2 parts of pyridine, and the reaction was conducted under reflux for 2 hours. Thereafter, the product was treated similarly as in Example 20 to obtain 20.2 parts of white crystals of 6-fluoro-4-oximino-1-ethoxycarbonyl-1,2,3,4-tetrahydroquinoline. This product showed a melting point of 122°–124° C. when measured by the method specified in the Japanese Pharmacopeia, and the results of its elemental analysis were as follows:

Elemental Analysis:

| | C | H | F | N |
|---|---|---|---|---|
| Calculated: | 57.14 | 5.16 | 7.54 | 11.11 |
| Found: | 57.18 | 5.18 | 7.55 | 11.08. |

EXAMPLE 22

Similarly as in Example 20, 6-bromo-4-oxo-1,2,3,4-tetrahydroquinoline was reacted with methyl chloroformate and subsequently converted into the oxime thereby obtaining white crystals of 6-bromo-4-oximino-1-methoxycarbonyl-1,2,3,4-tetrahydroquinoline. The properties of the product are gven in Table 2 below.

EXAMPLE 23

Similarly as in Example 21, 6-fluoro-4-oxo-1,2,3,4-tetrahydroquinoline was reacted with methyl chloroformate and subsequently converted into the oxime thereby obtaining white 6-fluoro-4-oximino-1-methoxycarbonyl-1,2,3,4-tetrahydroquinoline. The properties of the product are given in Table 2.

EXAMPLE 24

Similarly as in Example 20, 6-chloro-4-oxo-1,2,3,4-tetrahydroquinoline was reacted with ethyl chloroformate and subsequently converted into the oxime thereby obtaining 6-chloro-4-oximino-1-ethoxycarbonyl-1,2,3,4-tetrahydroquinoline. The properties of the product are given in Table 2.

EXAMPLE 25

Similarly as in Example 20, 6-chloro-4-oxo-1,2,3,4-tetrahydroquinoline was reacted with isopropyl chloroformate and subsequently converted into the oxime thereby obtaining 6-chloro-4-oximino-1-isopropoxycarbonyl-1,2,3,4-tetrahydroquinoline. The properties of the product are given in Table 2.

EXAMPLE 26

Similarly as in Example 20, 6-bromo-4-oxo-1,2,3,4-tetrahydroquinoline was reacted with isopropyl chloroformate and subsequently converted to the oxime thereby obtaining the desired 6-bromo-4-oximino-1-isopropoxycarbonyl-1,2,3,4-tetrahydroquinoline. The properties of the product are given in Table 2.

TABLE 2

| Example No. | Compound | Appearance | Melting Point (°C.) |
|---|---|---|---|
| 22 | 6-bromo-4-oximino-1-methoxycarbonyl-1,2,3,4-tetrahydroquinoline | White crystal | 155.5–158.5 |
| 23 | 6-fluoro-4-oximino-1-methoxycarbonyl-1,2,3,4-tetrahydroquinoline | " | 145–148 |
| 24 | 6-chloro-4-oximino-1-ethoxycarbonyl-1,2,3,4-tetrahydroquinoline | " | 112–113 |
| 25 | 6-chloro-4-oximino-1-isopropoxycarbonyl-1,2,3,4-tetrahydroquinoline | " | 165.5–167.5 |
| 26 | 6-bromo-4-oximino-1-isopropoxycarbonyl-1,2,3,4-tetrahydroquinoline | " | 160–162.5 |

EXAMPLE 27

Synthesis of 6-fluoro-4-oximino-1-formyl-1,2,3,4-tetrahydroquinoline 16.51 parts of 6-fluoro-4-oxo-1,2,3,4-tetrahydroquinoline and 150 parts of formic acid (purity of 98% or higher) were mixed and reacted under reflux with stirring for 3 hours.

The reaction mixture was distilled under reduced pressure to remove the excess formic acid, 100 ml of ethanol was added to the residue and heated to dissolve it. After cooling, the precipitated crystals were filtered out, and dried to obtain 16.2 parts of 6-fluoro-4-oxo-1-formyl-1,2,3,4-tetrahydroquinoline.

Then, the above product was dissolved in 250 ml of ethanol, to which were added 15.0 parts of hydroxylamine hydrochloride and 17.0 parts of pyridine, and the reaction was conducted under reflux for 2 hours.

The reaction mixture was poured into one liter of water, filtered out, washed with water, dried and then recrystallized from ethanol to obtain 16.1 parts of white cyrstals of 6-fluoro-4-oximino-1-formyl-1,2,3,4-tetrahydroquinoline.

This product showed a melting point of 175.5°–176.5° C. when measured by the method specified in the Japanese Pharmacopeia, and the results of its elemental analysis were as follows:

Elemental Analysis:

| | C | H | F | N |
|---|---|---|---|---|
| Calculated: | 57.69 | 4.33 | 9.13 | 13.46 |
| Found: | 57.63 | 4.30 | 9.17 | 13.48 |

EXAMPLE 28

Synthesis of 6-bromo-4-oximino-1-acetyl-1,2,3,4-tetrahydroquinoline 22.61 parts of 6-bromo-4-oxo-1,2,3,4-tetrahydroquinoline and 13.3 parts of acetic anhydride were mixed and reacted at 90° C. with stirring for 3 hours.

The reaction mixture was poured into 500 ml of water, and the precipitated crystals were filtered out, washed with water, and dried to obtain 23.9 parts of 6-bromo-4-oxo-1-acetyl-1,2,3,4-tetrahydroquinoline.

Then, the above product was dissolved in 350 ml of ethanol, to which were added 14.6 parts of hydroxylamine hydrochloride and 16.1 parts of pyridine, and the reaction was effected under reflux for 2 hours. Thereafter, the mixture was treated as in Example 27 to obtain 24.1 parts of white crystals of 6-bromo-4-oximino-1-acetyl1,2,3,4-tetrahydroquinoline.

This product showed a melting point of 200°–202.5° C. when measured by the method specified in the Japanese Pharmacopeia, and the results of the elemental analysis were as follows:

Elemental Analysis:

| | O | H | Br | N |
|---|---|---|---|---|
| Calculated: | 46.64 | 3.89 | 28.27 | 9.89 |
| Found: | 46.67 | 3.84 | 28.24 | 9.92 |

EXAMPLE 29

Synthesis of 6-fluoro-4-oximino-1-propionyl-1,2,3,4-tetrahydroquinoline 16.51 parts of 6-fluoro-4-oxo-1,2,3,4-tetrahydroquinoline, 11.9 parts of pyridine and 100 ml of dioxane were mixed and 12.0 parts of propionyl chloride was added dropwise to the stirred mixture while the temperature was maintained at 0°–5° C.

The reaction mixture was poured into one liter of water, and the precipitated crystals were filtered out, washed with water and then with petroleum ether, and dried to obtain 20.4 parts of 6-fluoro-4-oxo-1-propionyl-1,2,3,4-tetrahydroquinoline.

Then, the above product was converted to the oxime as in Example 27, thereby obtaining 19.5 parts of white 6-fluoro-4-oximino-1-propionyl-1,2,3,4-tetrahydroquinoline. This product showed a melting point of 126.5°–128° C. when measured by the method specified by the Japanese Pharmacopeia, and the results of its elemental analysis were as follows:

Elemental Analysis:

| | C | H | F | N |
|---|---|---|---|---|
| Calculated: | 61.02 | 5.51 | 8.05 | 11.86 |

| | C | H | F | N |
|---|---|---|---|---|
| Found: | 61.04 | 5.55 | 8.02 | 11.82 |

EXAMPLES 30–36

In each example, the desired product was obtained by the method similar to that in Example 29, except that the propionyl chloride was replaced by the corresponding acid chloride. The properties of the products are given in Table 3 below.

EXAMPLE 37

Synthesis of 6-fluoro-4-oximino-1-dimethylcarbamoyl-1,2,3,4-tetrahydroquinoline (a) 33.0 parts of 6-fluoro-4-oxo-1,2,3,4-tetrahydroquinoline and 200 parts of dioxane were mixed, and 39.6 parts of phosgene were introduced to the stirred mixture over about 30 minutes while the temperature was maintained at 20°–25° C. After the introduction, the temperature was raised gradually, and the reaction was effected at 40°–45° C. for 2.5 hours, after which the temperature was further raised to 70° C., nitrogen gas was passed through the mixture, and the solvent (dioxane) was distilled off under reduced pressure. Petroleum ether was added to the residue followed by filtration, washing and drying, and there was obtained 43.7 parts of 6-fluoro-4-oxo-1-chloroformyl-1,2,3,4-tetrahydroquinoline.

(b) 2.3 Parts of the above product were dissolved in 30 ml of dioxane, and this solution was added dropwise to 10 ml of dioxane solution containing 1.5 parts of dimethylamine while the temperature was maintained at 0°–5° C. After the addition, stirring was continued at room temperature for 4 hours.

The reaction mixture was poured into water, and the precipitated crystals were filtered out, washed with water and then with petroleum ether, dried and recrystallized from a mixed solvent of ethanol-n-hexane to obtain 2.0 parts of 6-fluoro-4-oxo-1-dimethylcarbamoyl-1,2,3,4-tetrahydroquinoline. This product was dissolved in 30 ml of ethanol, to which were added 1.8 parts of hydroxylamine hydrochloride and 1.9 parts of pyridine, and the reaction was conducted under reflux for 2 hours. Thereafter, the mixture was treated as in Example 27 to obtain 2.0 parts of white crystals of 6-fluoro-4-oximino-1-dimethylcarbamoyl-1,2,3,4-tetrahydroquinoline. This product showed a melting point of 147°–149.5° C. when measured by the method specified in the Japanese Pharmacopeia, and the results of its elemental analysis were as follows:

Elemental Analysis:

| | C | H | F | N |
|---|---|---|---|---|
| Calculated: | 57.37 | 5.58 | 7.57 | 16.73 |

| | C | H | F | N |
|---|---|---|---|---|
| Found: | 57.34 | 5.53 | 7.56 | 16.78 |

EXAMPLE 38

The 6-fluoro-4-oxo-1-chloroformyl-1,2,3,4-tetrahydroquinoline obtained in Example 37 (a) was treated similarly as in Example 37 (b) except that the dimethylamine was replaced by aniline, to obtain the desired product. The properties of the product are given in Table 3.

EXAMPLE 39

Synthesis of 6-bromo-4-oximino-1-methylcarbamoyl-1,2,3,4-tetrahydroquinoline (a) 45.2 Parts of 6-bromo-4-oxo-1,2,3,4-tetrahydroquinoline and 200 parts of dioxane were mixed, and 39.4 parts of phosgene was introduced to the stirred mixture while the temperature was maintained at 20°–25° C. over about 30 minutes. After the introduction, the reaction was effected at 40°–45° C. for 2.5 hours, and thereafter the mixture was treated as in Example 37 (a) to obtain 55.9 parts of 6-bromo-4-oxo-1-chloroformyl-1,2,3,4-tetrahydroquinoline.

(b) 2.9 parts of the above compound were dissolved in 30 ml of dioxane, and this solution was added dropwise to 10 ml of dioxane solution containing 1.1 parts of monomethylamine while the temperature was maintained at 0°–5° C. After the addition, stirring was continued at room temperature for 4 hours, and thereafter the mixture was treated as in Example 37 (b) to obtain 2.4 parts of 6-bromo-4-oxo-1-methylcarbamoyl-1,2,3,4-tetrahydroquinoline.

Then, the above product was treated smilarly as in Example 27 to convert it into the oxime, thereby obtaining 2.3 parts of white 6-bromo-4-oximino-1-methylcarbamoyl-1,2,3,4-tetrahydroquinoline. The product showed a melting point of 206.5° C. (dec.) when measured by the method specified in the Japanese Pharmacopeia, and the results of its elemental analysis were as follows:

Elemental Analysis:

| | C | H | Br | N |
|---|---|---|---|---|
| Calculated: | 44.30 | 4.03 | 26.85 | 14.09 |
| Found: | 44.28 | 4.05 | 26.81 | 14.11 |

EXAMPLE 40

The 6-bromo-4-oxo-1-chloroformyl-1,2,3,4-tetrahydroquinoline obtained in Example 39 (a) was treated similarly as in Example 39 (b) except that the monomethylamine was replaced by dimethylamine, to obtain the desired product. The properties of the product are given in Table 3.

TABLE 3

| Example No. | Compound | Appearance | Melting Point (°C.) |
|---|---|---|---|
| 30 | 6-bromo-4-oximino-1-propionyl-1,2,3,4-tetrahydroquinoline | White crystal | 151.5–152.5 |
| 31 | 6-bromo-4-oximino-1-isobutyryl-1,2,3,4-tetrahydroquinoline | " | 195–197 |
| 32 | 6-fluoro-4-oximino-1-trimethylacetyl-1,2,3,4-tetrahydroquinoline | " | 211–212.5 |
| 33 | 6-bromo-4-oximino-1-hexanoyl-1,2,3,4-tetrahydroquinoline | " | 208.5–210.5 |
| 34 | 6-fluoro-4-oximino-1-benzoyl-1,2,3,4-tetrahydroquinoline | " | 185.5–187.5 |

TABLE 3-continued

| Example No. | Compound | Appearance | Melting Point (°C.) |
|---|---|---|---|
| 35 | 6-bromo-4-oximino-1-(2,4-dichlorobenzoyl)-1,2,3,4-tetrahydroquinoline | " | 178.5–181.5 |
| 36 | 6-bromo-4-oximino-1-cinnamoyl-1,2,3,4-tetrahydroquinoline | " | 208.5–210.5 |
| 38 | 6-fluoro-4-oximino-1-phenylcarbamoyl-1,2,3,4-tetrahydroquinoline | " | 159.5 (dec.) |
| 40 | 6-bromo-4-oximino-1-dimethylcarbamoyl-1,2,3,4-tetrahydroquinoline | " | 113–115 |

The compounds of this invention have strong antiedemic, diuretic and hypotensive effects and further hardly cause gastrointestinal disorder. By way of example, when the diuretic effect of the compounds obtained in Examples 3, 20, 23, 29 and 30 were tested in rats, each showed a diuretic effect about 4 times stronger than that of furosemide which was the control agent. Further, it was confirmed that their toxicity was negligible at dosages commonly employed in medical treatment.

What is claimed is:

1. A 4-oximino-1,2,3,4-tetrahydroquinoline derivative of the formula (I):

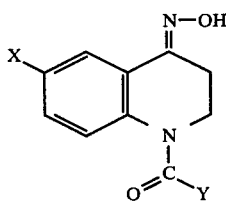

wherein X represents a halogen, and Y represents hydrogen, a straight-chain or branched-chain alkyl group of 1 to 9 carbon atoms, a trifluoromethyl group, a phenylmethyl group, a phenylethylene group, a pyridyl group, a straight-chain or branched-chain alkoxy group of 1 to 3 carbon atoms, an amino group substituted by an alky group of 1 to 2 carbon atoms, or a phenylamino group.

2. A 4-oximino-1,2,3,4-tetrahydroquinoline derivative according to claim 1 wherein X is chlorine, and Y is a straight chain or branched-chain alkyl group of 1–9 carbon atoms, a trifluoromethyl group, a phenylethylene group, a pyridyl group, a 1–2 carbon alkyl-substituted amino group, or a phenylamino group.

3. A 4-oximino-1,2,3,4-tetrahydroquinoline derivative according to claim 1, wherein X is fluorine or bromine, and Y is hydrogen, a straight-chain or branched-chain 1–9 carbon alkyl group, a phenylmethylene group, a 1–2 carbon alkyl-substituted amino group, or a phenylamino group.

4. A 4-oximino-1,2,3,4-tetrahydroquinoline derivative according to claim 1, wherein X is fluorine, chlorine, or bromine, and Y is a straight-chain or branched-chain 1–3 carbon alkoxy group.

5. A 4-oximino-1,2,3,4-tetrahydroquinoline derivative according to claim 1, which is 6-chloro-4-oximino-1-propionyl-1,2,3,4-tetrahydroquinoline, 6-chloro-4-oximino-1-methoxycarbonyl-1,2,3,4-tetrahydroquinoline, 6-fluoro-4-oximino-1-methoxycarbonyl-1,2,3,4-tetrahydroquinoline, 6-fluoro-4-oximino-1-propionyl-1,2,3,4-tetrahydroquinoline or 6-bromo-4-oximino-1-propionyl-1,2,3,4-tetrahydroquinoline.

* * * * *

UNITED STATES PATENT AND TRADEMARK OFFICE
CERTIFICATE OF CORRECTION

PATENT NO. : 4,421,919
DATED : December 20, 1983
INVENTOR(S) : Susumu JINBO, ET AL.

It is certified that error appears in the above—identified patent and that said Letters Patent is hereby corrected as shown below:

In the first column of the cover page, under the heading "Inventors:", the following corrections should appear:

Change "Kashima," to -- Kashima; Ei Mochida; Kazuo Yamaguchi,"

After "Japan" add -- ; Haruo Ohnishi, Chiba-ken, Japan; Yasuo Suzuki, Saitama, Japan; and Hiroshi Kosuzume, Kanagawa-ken, Japan --.

Signed and Sealed this

Twentieth Day of March 1984

[SEAL]

Attest:

GERALD J. MOSSINGHOFF

Attesting Officer

Commissioner of Patents and Trademarks

UNITED STATES PATENT AND TRADEMARK OFFICE
CERTIFICATE OF CORRECTION

PATENT NO. : 4,421,919

DATED : December 20, 1983

INVENTOR(S) : Susumu JINBO, et al.

It is certified that error appears in the above—identified patent and that said Letters Patent is hereby corrected as shown below:

Column 2, line 34, change "P-propiolactone" to
-- β-propiolactone --.

Signed and Sealed this

Fifth Day of June 1984

[SEAL]

Attest:

GERALD J. MOSSINGHOFF

Attesting Officer

Commissioner of Patents and Trademarks